(12) United States Patent
Garcia et al.

(10) Patent No.: US 9,134,223 B2
(45) Date of Patent: Sep. 15, 2015

(54) MODIFICATION OF A FLOW CELL TO MEASURE ADSORPTION KINETICS UNDER STAGNATION POINT FLOW AND DEVELOPMENT OF A SETUP CORRECTION PROCEDURE FOR OBTAINING ADSORPTION KINETICS AT THE STAGNATION POINT

(75) Inventors: Carlos Garcia, San Antonio, TX (US); Maria Fernanda Mora, La Crescenta, CA (US); Mohammad Reza Nejadnik, Nijmegen (NL)

(73) Assignee: Board of Regents of the University of Texas System, Austin, TX (US)

( * ) Notice: Subject to any disclaimer, the term of this patent is extended or adjusted under 35 U.S.C. 154(b) by 196 days.

(21) Appl. No.: 13/634,208

(22) PCT Filed: Mar. 11, 2011

(86) PCT No.: PCT/US2011/028208
§ 371 (c)(1),
(2), (4) Date: Jan. 25, 2013

(87) PCT Pub. No.: WO2011/113007
PCT Pub. Date: Sep. 15, 2011

(65) Prior Publication Data
US 2013/0114080 A1     May 9, 2013

Related U.S. Application Data

(60) Provisional application No. 61/313,574, filed on Mar. 12, 2010.

(51) Int. Cl.
*G01N 21/01*      (2006.01)
*G01N 21/21*      (2006.01)
*G01N 21/05*      (2006.01)

(52) U.S. Cl.
CPC ............... *G01N 21/01* (2013.01); *G01N 21/05* (2013.01); *G01N 21/211* (2013.01)

(58) Field of Classification Search
CPC ...... G01N 21/05; G01N 21/211; G01N 21/01
USPC .......... 356/301, 318, 317, 246, 369, 364–367
See application file for complete search history.

(56) References Cited

U.S. PATENT DOCUMENTS

| | | | |
|---|---|---|---|
| 4,076,420 A * | 2/1978 | De Maeyer et al. | ............ 356/73 |
| 4,330,206 A | 5/1982 | Gausmann et al. | |

(Continued)

FOREIGN PATENT DOCUMENTS

| | | |
|---|---|---|
| CA | 2140373 | 8/1995 |
| EP | 1416565 | 6/2004 |

(Continued)

OTHER PUBLICATIONS

Curwen et al. "Adsorption kinetics in a dual-inlet channel flow cell: I. Cetyl pyridinium chloride on hydrophilic silica" Journal of Physical Chemistry, 2007, vol. 111, No. 33, pp. 12289-12304.

(Continued)

*Primary Examiner* — Michael A Lyons
*Assistant Examiner* — Violeta A Prieto
(74) *Attorney, Agent, or Firm* — Meyertons, Hood, Kivlin, Kowert & Goetzel, P.C.; Eric B. Meyertons (57) ABSTRACT

This application describes a flow cell to perform experiments under well-controlled hydrodynamic conditions. The resulting cell enables combining the advantages of in-situ spectroscopic ellipsometry with stagnation point flow conditions. An additional advantage is that the proposed cell features a fixed position of the "inlet conduit" with respect to the substrate, thus facilitating the alignment of multiple substrates. Theoretical calculations were performed by computational fluid dynamics and compared with experimental data (adsorption kinetics) obtained for the adsorption of polyethylene glycol to silica under a variety of experimental conditions. Additionally, a simple methodology to correct experimental data for errors associated with the size of the measured spot and for variations of mass transfer in the vicinity of the stagnation point is herein introduced. The proposed correction method would allow researchers to reasonably estimate the adsorption kinetics at the stagnation point and quantitatively compare their results, even when using different experimental setups. The applicability of the proposed correction function was verified by evaluating the kinetics of protein adsorption under different experimental conditions.

18 Claims, 10 Drawing Sheets

(56) References Cited

U.S. PATENT DOCUMENTS

| | | | |
|---|---|---|---|
| 5,739,910 | A | 4/1998 | Castor |
| 6,937,341 | B1* | 8/2005 | Woollam et al. ............... 356/436 |
| 7,817,266 | B2* | 10/2010 | Pfeiffer et al. ................. 356/246 |
| 8,130,375 | B1* | 3/2012 | Pfeiffer et al. ................. 356/246 |
| 8,493,565 | B1* | 7/2013 | Pfeiffer et al. ................. 356/445 |
| 8,531,665 | B1* | 9/2013 | Pfeiffer et al. ................. 356/369 |
| 2003/0214654 | A1 | 11/2003 | Wei et al. |
| 2006/0005634 | A1 | 1/2006 | Schroeder et al. |
| 2006/0256332 | A1* | 11/2006 | Sandstrom .................... 356/317 |
| 2008/0204713 | A1* | 8/2008 | Indermuehle et al. .......... 356/72 |
| 2009/0027679 | A1* | 1/2009 | Pfeiffer et al. ................. 356/440 |
| 2009/0059230 | A1 | 3/2009 | Hermens |
| 2011/0097793 | A1 | 4/2011 | Suzuki et al. |

FOREIGN PATENT DOCUMENTS

| | | |
|---|---|---|
| EP | 2017601 | 1/2009 |
| WO | 94/11722 | 5/1994 |
| WO | 97/01087 | 1/1997 |
| WO | 2007/079196 | 7/2007 |
| WO | 2009/059014 | 5/2009 |

OTHER PUBLICATIONS

ISS brochure Total Internal Reflection Fluorescence (TIRF) Flow Cell, 2005.

Mora et al. "Determinaton of a setup correction function to obtain adsorption kinetic data at stagnation point flow conditions." Journal of Colloid and Interface Science, Feb. 13, 2010, 346 (2010), 208-215.

Wagberg et al. "The use of stagnation point adsorption reflectometry to study molecular interactions relevant to papermaking chemistry." Colloids and Surfaces A: Physicochemical and Engineering Aspects, Dec. 31, 1999, 159 (1999), 3-15.

Garcia et al. "Reflectometry applied to electrochemically generated phenoxy radical adsorption monitoring." Journal of Electroanalytical Chemistry, Dec. 31, 2002, 519(2002), 53-59.

International Search Report for PCT Application No. PCT/US2011/028208 issued Aug. 31, 2011.

Written Opinion for PCT Application No. PCT/US2011/028208 issued Aug. 31, 2011.

International Preliminary Report on Patentability for PCT Application No. PCT/US2011/028208 issued Sep. 18, 2012.

* cited by examiner

MODIFICATION OF A FLOW CELL TO MEASURE ADSORPTION KINETICS UNDER STAGNATION POINT FLOW AND DEVELOPMENT OF A SETUP CORRECTION PROCEDURE FOR OBTAINING ADSORPTION KINETICS AT THE STAGNATION POINT

BACKGROUND OF THE INVENTION

1. Field of the Invention

The invention generally relates to systems and methods for the analysis of absorption of molecules onto solid surfaces. More specifically, the invention relates to methods and systems that use optical methods (e.g. ellipsometry) to determine information related to the adsorption process.

2. Description of the Relevant Art

The adsorption of macromolecules, colloids, and bioparticles to solid surfaces has been widely reported in literature with studies that include different methodologies, surfaces, and applications. The time-dependence nature of the adsorption processes, as well as the significance of the initial steps for various biomedical and industrial applications, highlights the importance of kinetic studies. Regardless of the selected analytical technique to follow the process, there are two main experimental approaches to study adsorption kinetics of particles: batch and flow experiments. Batch experiments are generally performed by monitoring the depletion of adsorbate in a dispersion of sorbent particles. Although this approach is attractive due to its minimal instrumental requirements, it involves non-uniform hydrodynamic conditions, and is limited to slow adsorption processes (significantly slower than the mixing and separation time).

A more efficient way to study adsorption processes, particularly those involving shorter time-scales, is by flowing a solution of adsorbate over the sorbent surface. Several authors have pointed out the advantages of performing such studies in which the well-controlled hydrodynamic conditions allow accurate measurements, particularly regarding the initial stages of the adsorption/desorption phenomena. Various flow displacement geometries have been used for such adsorption studies. Among those, setups yielding stagnation point flow conditions are frequently used for measurement of adsorption kinetics. Stagnation point flow conditions may be obtained by perpendicular impinging a jet of solution to the sorbent surface through a cylindrical channel. The stagnation point is defined as the intersection of the symmetry axis of the cylinder with the surface. The main advantage of this arrangement is that the hydrodynamics of the mass flux at the stagnation point can be accurately described. Additionally, under stagnation conditions, information regarding the contribution of each component involved in the adsorption process can be obtained.

Stagnation point flow conditions have been used for adsorption studies in conjunction with several techniques such as microscopy, quartz crystal microgravimetry, evanescent wave light scattering, and reflectometry. Spectroscopic ellipsometry (SE) is also used for adsorption studies because it can provide real-time information regarding the kinetics of the adsorption process as well as the structure of the adsorbed layer for a broad range of materials and substrates. Ellipsometry is an optical technique that measures changes in the reflectance and phase difference between the parallel (RP) and perpendicular (RS) components of a polarized light beam upon reflection from a surface. The intensity ratio of RP and RS can be related to the ellipsometric angles ($\Psi$, amplitude and $\Delta$, phase difference as functions of wavelength or time) using Equation 1:

$$\tan(\Psi)e^{j\Delta} = \frac{R_P}{R_S} \qquad \text{Equation 1}$$

Spectroscopic ellipsometry allows the measurement of the ellipsometric angles as a function of the wavelength of the incident light beam. Because ellipsometry measures the ratio of two values originated by the same signal, the data collected are highly accurate and reproducible. The output values of ellipsometry are extremely sensitive to the thickness (down to the monolayer level), optical constants, and microstructure (such as surface roughness, index grading, and intermixing) of the films. This monolayer sensitivity is useful for real-time studies of film deposition, including the formation of layers of biological molecules on a wide variety of substrates. It is worth noticing that although dynamic adsorption studies performed by ellipsometry have been widely reported in literature, the flow conditions in these reports have not been properly characterized.

One common issue associated with the use of optical methods, such as reflectometry or ellipsometry, to perform adsorption kinetic studies is that these techniques typically underestimate the initial adsorption rate. The difference between the experimental and predicted values have been attributed to the fact that these instruments collect signals from a spot (few square millimeters) rather than an infinitesimal point (stagnation point). Therefore, the adsorption rates calculated based on these signals could be significantly smaller than the adsorption rates existing at the stagnation point. As a consequence, similar experiments performed with diverse experimental setups may render significantly different results (depending on the size of the measured area), making quantitative interlaboratory comparisons challenging.

SUMMARY OF THE INVENTION

Considering the aforementioned points, described herein is a characterized flow cell to perform ellipsometric adsorption studies under stagnation point flow conditions. Such a system and method has the advantages of combining ellipsometry with stagnation point flow conditions to perform dynamic adsorption studies; and providing a procedure to calculate a setup-specific correction function that allows correcting experimental kinetic data for errors associated with the size of the measured spot.

In one embodiment, a flow cell couplable to an ellipsometer, includes an inlet conduit comprising an exit port and an inlet port, wherein the inlet port is configured to receive a fluid containing an adsorbate during use. The flow cell also includes a substrate holder configured to couple to a substrate during use and a light inlet and a light outlet, optically couplable to a substrate coupled to the substrate holder. The inlet conduit is positioned such that fluid flows from the exit port toward the substrate during use and impinges the surface of a substrate, positioned in the substrate holder at a point substantially coincident with light striking the substrate from the light beam inlet. In an embodiment, the fluid exits the inlet substantially perpendicular to the substrate during use. The distance of the inlet exit port from the substrate as well as the position with respect to the substrate and the size of the tubes may be adjustable.

In an embodiment, an ellipsometer includes:
a light source;
a substrate holder configured to couple to a substrate during use, wherein the light source is optically couplable to a substrate coupled to the substrate holder;
an inlet conduit having an exit port and an inlet port, wherein the inlet port is configured to receive a fluid containing an adsorbate during use; and
a detector optically couplable to the substrate holder, wherein the detector is optically coupled to receive light from the light source that is reflected from the surface.

The inlet conduit is positioned such that fluid flowing from the exit port to the substrate during use impinges the surface of a substrate, positioned in the substrate holder, at a point substantially coincident with light striking the substrate from the light source.

A method of studying the adsorption of an adsorbate an a substrate includes sending a fluid containing the adsorbate toward a surface of a substrate, such that at least a portion of the fluid contacts the substrate. Light is sent from a light source toward the position on the surface that is contacted by the fluid. The adsorption is studied by measuring the change in optical properties of light reflected from the substrate at the position on the surface that is contacted by the fluid.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Figure 1:
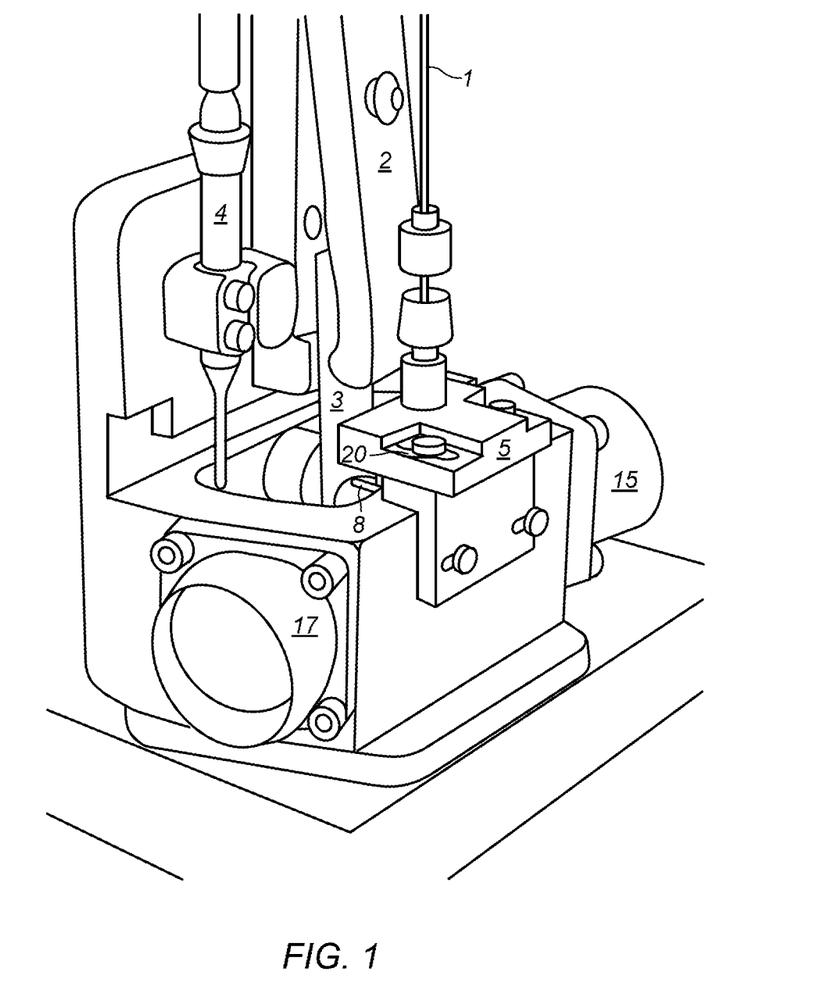
FIG. 1 depicts a projection view of a flow cell.
Figure 2:
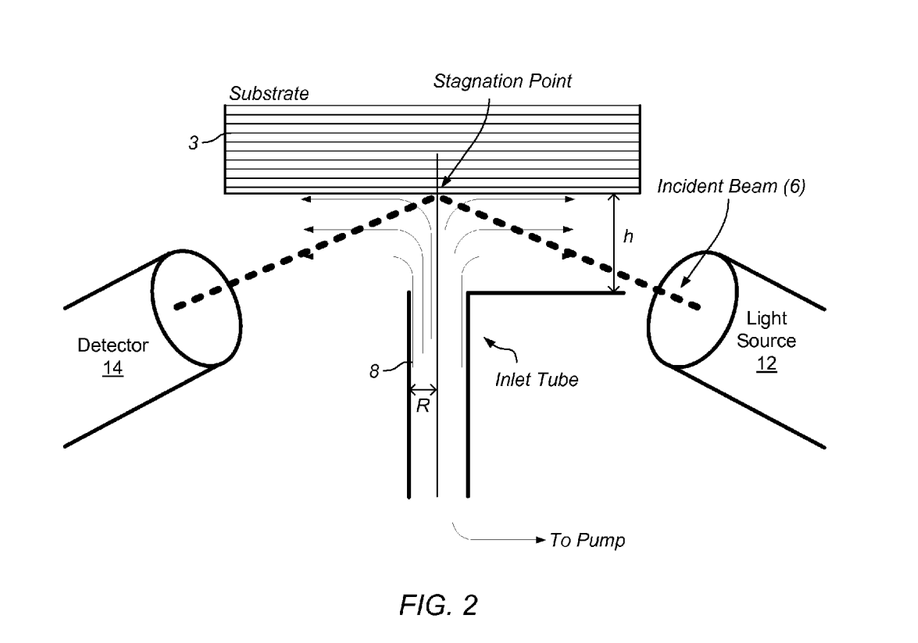
FIG. 2 depicts a cross-sectional top view of the flow cell of FIG. 1.

In one embodiment, dynamic adsorption may be performed in a flow cell configured for spectroscopic ellipsometry as depicted in FIG. 1. A flow cell includes an inlet conduit 1, substrate holder 2, drain 4, and inlet conduit positioner 5. Inlet conduit may be a straight tube or may be bent to at an angle. An exit port of inlet conduit 1 is positioned such that at least a portion of fluid flowing from the exit port 8 is directed toward the surface of substrate 3 coupled to substrate holder 2. As used herein the phrase "toward the surface" refers to the exit port being positioned such that an angle between the exit port of the inlet conduit with respect to the surface is greater than 0, or greater than 10, or greater than 30, or greater than 45, or about 90. The flow cell includes light inlet 15 and light outlet 17. FIG. 2 depicts a cross-sectional top view of exit port 8 positioned toward the surface of substrate 3. As shown, fluid exiting exit port 8 impinges substrate 3 creating a stagnation point. An incident beam 6 of light is directed to the surface from light source 12 at the point on the surface that the fluid exiting exit port 8 contacts the surface.

In an embodiment, a flow cell, such as a flow cell depicted in FIG. 1, is coupled to an ellipsometer. The ellipsometer may be a spectral ellipsometer. In one embodiment, an ellipsometer includes: a light source; a substrate holder configured to couple to a substrate during use, wherein the light source is optically couplable to a substrate coupled to the substrate holder; an inlet conduit comprising an exit port and an inlet port, wherein the inlet port is configured to receive a fluid containing an adsorbate during use; and a detector optically couplable to the substrate holder, wherein the detector is optically coupled to receive light from the light source that is reflected from the surface. The ellipsometer is set up such that the inlet conduit is positioned such that fluid flowing from the exit port is directed toward the surface of the substrate impinges the surface of a substrate, at a point substantially coincident with light striking the substrate from the light source.

The inlet port of inlet conduit 1 may be connected to a pump. One or more valves may be coupled to the pump and the inlet conduit to facilitate switching between incoming fluids. The distance from the end of exit port 8 of inlet conduit 1 to the surface of substrate 3 may be fixed or may be adjustable. Inlet conduit positioner 5 may be used to alter the distance of exit port 8 from the substrate and/or adjust the angle between exit port 8 of inlet conduit 1 with respect to the surface of substrate 3. The angle can be adjusted by rotating the inlet conduit positioner 5 through slot 20. As depicted in FIG. 2, the adsorbate fluid may impinge the surface of the substrate with an angle of incidence equal to 90 (with respect to the surface). Other angles of incidence for the fluid may be chosen, as long as the fluid is directed toward the surface. The described embodiments enable monitoring of the adsorption process in-situ and in real time. An additional advantage of the flow cells, such as the flow cell of FIG. 1, allows the adjustment of the distance between the inlet conduit and the substrate providing versatility to the design. Furthermore, the fixed position of the inlet conduit with respect to the substrate (which also has a fixed position) after adjustment, facilitates the alignment of different substrates and the optical components.

The fluid dynamics of a flow cell may be modeled using two parallel solid plates separated by a distance h. One of the plates is assigned to the substrate in which the adsorption process takes place, and used as a reference point (0, 0). The second plate (located at z=h) was assigned to the end of the inlet conduit (of radius R), which delivers the solution containing the adsorbate. The flow is developed in the cell, and the fluid moved to an outflow region, located away from the symmetry axis. For all the calculations, a ratio of h/R equal to 2.8 was considered and all the fluids were assumed to be Newtonian and incompressible. The ratio h/R is one parameter that determines the flow distribution and the adsorption kinetics. The flow of fluid along the cell can be characterized using the Reynolds number (Re), a dimensionless parameter defined as:

$$Re = \frac{\rho R U}{\eta} \quad \text{Equation 2}$$

where $\rho$ and $\eta$ are the density and the viscosity of the fluid respectively, R is the radius of the tube, and U is the mean fluid velocity. The Reynolds number, which characterizes the tendency of a fluid to develop turbulence or to flow with a laminar regime, was varied in the 2-50 range. This range is significantly smaller than the value of Re at which the flow changes from laminar to turbulent (Re>2000). Under the specified conditions, the fluid flow remains in a laminar regime and the flow can be described using the steady-state Navier-Stokes equation and the continuity equation. Due to the axisymmetrical design of the cell, these equations can be expressed in cylindrical coordinates r and z, with the form $$-\frac{\partial p}{\partial r} + \eta\left(\frac{1}{r}\frac{\partial}{\partial r}\left(r\frac{\partial u_r}{\partial r}\right) - \frac{\partial^2 u_r}{\partial z^2} - \frac{u_r}{r^2}\right) = 0 \quad \text{Equation 3}$$

$$-\frac{\partial p}{\partial z} + \eta\left(\frac{1}{r}\frac{\partial}{\partial r}\left(r\frac{\partial u_z}{\partial r}\right) + \frac{\partial^2 u_z}{\partial z^2}\right) = 0 \quad \text{Equation 4}$$

$$\frac{1}{r}\frac{\partial}{\partial r}(ru_r) + \frac{\partial u_z}{\partial z} = 0 \quad \text{Equation 5}$$

where $u_r$ is the radial component of the fluid velocity, p is the pressure, and $u_z$ is the axial component of the fluid velocity. Coordinates were non-dimensionalized with respect to the radius R and the components of the fluid velocity were referred to the mean velocity U. The fluid flow at the exit of the tube was assumed to show a parabolic profile, accordingly with a developed Poiseuille flow. With this assumption, the boundary conditions required to solve Equation 3 to Equation 5 can be formulated as:

$$u_r = u_z = 0 \text{ at the solid surfaces of the cell} \quad \text{Equation 6}$$

$$u_r = 0, u_z = U(1-r^2) \text{ at the surface of} \quad \text{Equation 7}$$
$$\text{the plate located at } z = 0$$

$$\frac{\partial u_z}{\partial r} = 0 \text{ in the symmetry axis} \quad \text{Equation 8}$$

$$u_z = 0 \text{ at the outflow region of the cell} \quad \text{Equation 9}$$

The numerical solutions for the fluid flow equations were obtained using the finite element method, as implemented in the COMSOL Multiphysics software. A mesh consisting of 4000 quadrilateral elements and 4141 points was constructed along the geometry of the model cell. At each point, a solution was approximated with a low order polynomial, and was further refined through a number of iterations. Close to the surface of the plate located at z=0, the radial and axial components of the fluid velocity can be approximated by the analytical expressions described in Equation 10 and Equation 11, $$u_r = \alpha r z \quad \text{Equation 10}$$

$$u_z = \alpha z^2 \quad \text{Equation 11}$$

where $\alpha$ is a flow intensity dimensionless parameter that is constant for a certain cell geometry and flow rate. The proposed approach was validated by comparing the results obtained using different geometries. In all cases, identical solutions were achieved.

In order to verify the consistency of obtained data in the proposed experimental setup with the values expected for adsorption at the stagnation point flow, the liquid cell used here was characterized by studying the adsorption kinetics of polyethylene glycol (PEG) to silica according to a procedure developed by Dijt et al. *Colloids Surf. A* 51 (1990) 141, which is incorporated herein by reference. Then, theoretical calculations were performed by computational fluid dynamics and compared with the experimental data obtained for the adsorption of PEG in order to determine the correction function needed for the geometry of our cell. Finally, the adsorption kinetics of two proteins were studied to demonstrate the applicability of the correction function to different analytes.

All chemicals were analytical reagent grade and used as received. All aqueous solutions were prepared using 18 MΩ·cm water (NANOpure Diamond, Barnstead; Dubuque, Iowa). Monodisperse polyethylene glycol was purchased from Polymer Laboratories (Amherst, Mass.) and used without further purification. Stock solutions of PEG were prepared by dissolving a known amount of solid material in DI water. Catalase (CAT) from bovine liver was purchased as a lyophilized powder (2-5 Ug$^{-1}$) from Sigma Aldrich (Saint Louis, Mo.) and kept at −20 C until used. Bovine Serum Albumin (BSA), fraction V (Heat-Shock Treated) was purchased from Fisher Scientific (Fair Lawn, N.J.) and kept at −4 C until used. Citrate buffer (10 mM) was selected as the background electrolyte because it provides high buffer capacity ($pK_{a1}$=3.13, $PK_{a2}$=4.76, $pK_{a3}$=6.4) around the isoelectric point (IEP) of the proteins (IEPCAT=5.4 and IEPBSA=4.7). The pH of the solutions was adjusted using either 1 M NaOH or 1 M HCl (Fisher Scientific; Fair Lawn, N.J.) and measured using a glass electrode and a digital pH meter (Orion 420A+, Thermo; Waltham, Mass.). Stock solutions of proteins were prepared by dissolving a known amount of protein in 10 mM citrate buffer. Other protein solutions were prepared by diluting the corresponding amount of stock in citrate buffer. Table 1 summarizes the corresponding molecular weights (Mw), ratio of weight to number molecular weight, and diffusion coefficients of the selected polymers and proteins. All experiments were performed using <111> Si/SiO$_2$ wafers (Sumco; Phoenix, Ariz.) as substrates. Before each experiment, Si/SiO$_2$ substrates were cleaned in a 1:1 mixture of HCl:H$_2$O$_2$ for 10 minutes at 80° C., rinsed thoroughly with water, and immersed in DI water until used to avoid contamination.

TABLE 1

|  | Molecular weight | $M_W/M_N$ | D ($10^{-7}$ cm$^2$ s$^{-1}$) |
|---|---|---|---|
| PEG | 278,100 | 1.05 | 1.36 |
| PEG | 93,000 | 1.06 | 2.50 |
| PEG | 8,730 | 1.05 | 9.34 |
| Catalase | 250,000 | — | 4.00 [74] |
| Bovine Serum Albumin | 66,000 | — | 5.93 [74] |

Both, the characterization of the substrates as well as the dynamic adsorption experiments, were performed at room temperature using a variable angle spectroscopic ellipsometer (WVASE, J.A. Woollam Co; Lincoln, Nebr.). Spectroscopic ellipsometry has proven suitable to study adsorption processes, and provides useful information about the optical constants and structure of the adsorbed film. Dynamic adsorption experiments were performed in the modified cell which was mounted directly on the vertical base of the ellipsometer. In all experiments, the variation of Ψ and Δ as a function of time was determined at an angle of incidence of 70°, as defined by the inlet/outlet of the UV fused-silica windows. Considering that the adsorption of PEG onto silica is a rather fast process, only one wavelength (650 nm) was used in order to increase the data acquisition rate and to determine the initial adsorption rate (($d\Gamma/dt$)$_{t\to 0}$) more accurately. The collected data were modeled using the WVASE software package (J.A. Woollam Co; Lincoln, Nebr.). Experimental results were interpreted using a model consisting of three uniaxial layers with optical axes parallel to the substrate surface. The dielectric functions of the substrates were described by a layer of Si (bulk; d=1 mm) and a layer of SiO$_2$ (d~2.5±0.5 nm). The adsorbed layers were described using a Cauchy parameterization model, according to Equation 12, where A, B, and C are computer-calculated fitting parameters, and λ is the wavelength of the incident light beam. The values of A, B, and C for each analyte were selected in such a way that the refractive indexes match the values reported in literature.

$$n_{(\lambda)} = A + \frac{B}{\lambda^2} + \frac{C}{\lambda^4} \qquad \text{Equation 12}$$

The Cauchy constants as well as the refractive indexes are summarized in Table 2. In agreement with previous reports, the extinction coefficient of all the adsorbates used in this study was considered to be zero. The mean square error (MSE, performed with a built-in function in WVASE) was used to quantify the difference between the experimental and model generated data.

TABLE 2

|  | A | B | C | $n_{650\,nm}$ | dn/dc |
|---|---|---|---|---|---|
| PEG | 1.34 | 0.01 | 0 | 1.362 [1] | 0.136 [1, 56] |
| Proteins | 1.44 | 0.01 | 0 | 1.465 [35] | 0.180 [55, 57] |

Prior to each adsorption experiment, spectroscopic scans were performed for a clean strip of silicon wafer mounted in the cell in order to determine the thickness of the SiO$_2$. This procedure allowed verifying the thickness of each substrate; therefore improving the accuracy of the calculation of the adsorbed layer. Then, the dynamic experiment was initiated by pumping water through the cell (~5 min) to measure the baseline. Next, the valve was switched, adsorbate solution was introduced, and the adsorption process started. After the process reached the corresponding equilibrium and no significant change in the signal was observed, the dynamic scan was stopped, and a more accurate spectroscopic scan was collected in the 300-850 nm range (with 10 nm steps). This scan was used to verify the thickness of the adsorbed layer.

The adsorbed amount (Γ, expressed in mg·m$^{-2}$) was calculated using Equation 13, $$\Gamma = \frac{d(n - n_0)}{(dn/dc)} \qquad \text{Equation 13}$$

where n and n$_0$ are the refractive index of the adsorbed layer (See Table 2) and the ambient (H$_2$O), respectively. In accordance with previous reports, a constant refractive index increment was considered for the adsorbed layers (See Table 2). Experiments performed in this way provided data for calculating the initial adsorption rate (($d\Gamma/dt$)$_{t\to 0}$) and the saturation adsorbed amount (Γ$_{SAT}$). These values were calculated for adsorption of PEG for different polymer concentrations, Reynolds numbers, and molecular weights as well as for adsorption of proteins.

The rate of adsorption at the solid/liquid interface is generally considered to include three steps: transport of the solute molecules from the bulk to the interface, attachment to the surface, and relaxation on the surface. When perfect sink boundary conditions are present (concentration at the surface is zero) and in the absence of a barrier, the flux of solute (J) towards the surface can be described by Equation 14:

$$J = 0.776 v^{1/3} R^{-1} (\alpha Re)^{1/3} D^{2/3} C \qquad \text{Equation 14}$$

where v is the kinematic viscosity of the solvent, R the inner radius of the tube through which the solution enters the cell (0.381 mm), D the diffusion coefficient of the studied adsorbate and, C is the concentration of the solute in the bulk.

It is also worth considering that, depending on the interactions involved (van der Waals, electrostatic, polymer bridging, or steric repulsion), solutes have a certain probability of attaching to the surface. This probability is represented by the efficiency factor (β) which relates the flux of adsorbate (J) to the adsorption rate (($d\Gamma/dt$)$_{t\to 0}$) according to Equation 15. Other denominations commonly used in the literature to refer to this factor are retardation factor or free surface area fraction.

$$\left(\frac{d\Gamma}{dt}\right)_{t\to 0} = \beta J \qquad \text{Equation 15}$$

Under perfect sink boundary conditions, which can exist when the adsorbate has a high affinity for the sorbent surface, this probability equals one. This will likely be the case for adsorption of neutral polymers such as PEG. As a consequence, in these systems, the initial rate of adsorption should be equal to the maximum rate of mass transfer from the bulk (J).

In order to demonstrate that the experimental setup presented in this study enables the formation of a stagnation point and that the adsorption process can be described by Equation 14, two different approaches (one theoretical and one experimental) were taken. The results of each strategy are herein discussed and compared. Subsequently, a methodology to correct the obtained kinetic parameters to account for the size of the measured spot is proposed.

Figure 3:
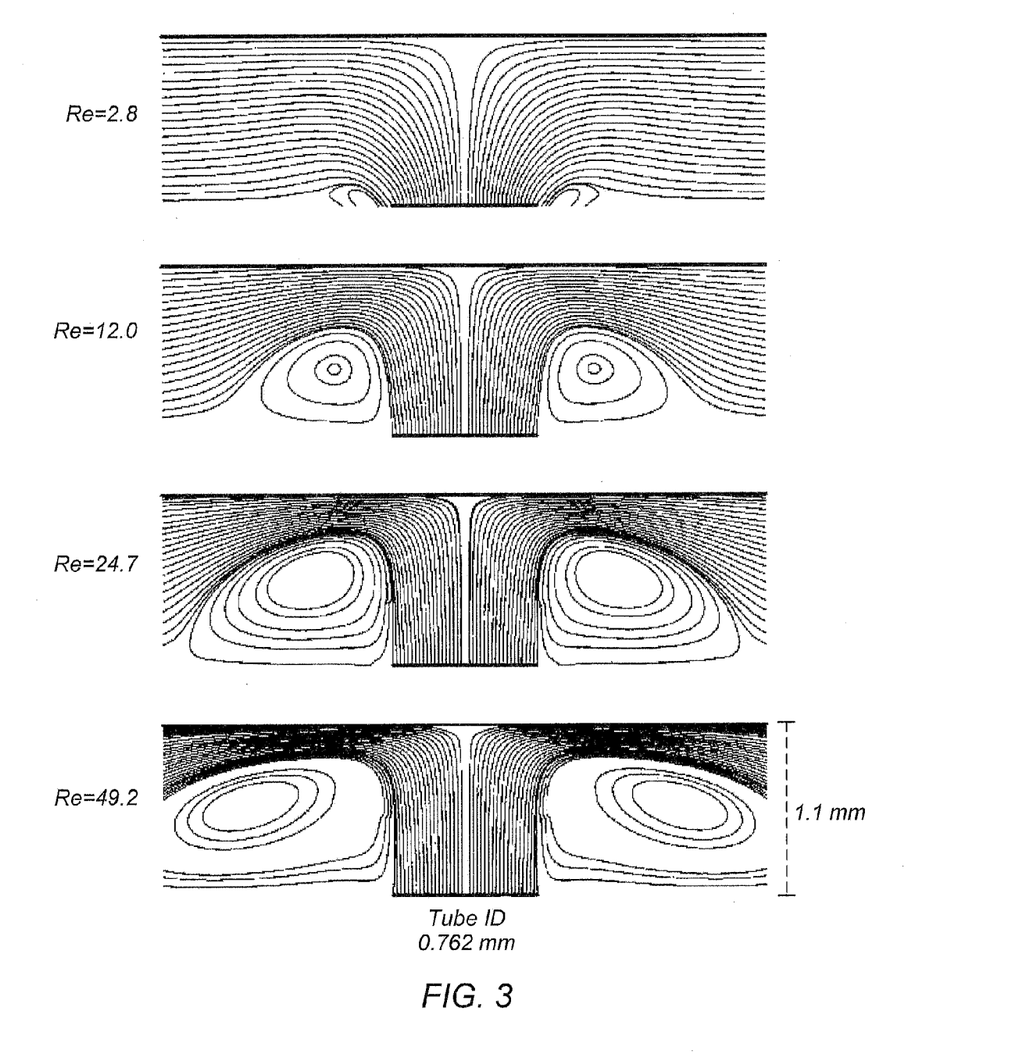
FIG. 3 shows the velocity profiles of various flow cell configurations.

Initially, the development of the flow fields in the cell was investigated. FIG. 3 shows the velocity profiles for Re of 2.8, 12.0; 24.7, and 49.2. The streamlines can be interpreted as the path of fluid-on the cell so the line tangent to the streamline represents the direction of the fluid velocity vector at a given point in space. As can be observed in FIG. 3, characteristic parabolic field lines around the point where the flow intersects with the substrate are developed, supporting the presence of a stagnation point. It is also noted that at low Re, the streamline pattern is typical of a stagnation point (hyperbolic) while the streamlines slightly deviate from hyperbolas at high Re. This behavior observed at high Re leads to a vortex formation away from the stagnation point. However, its presence should not affect the adsorption process because it is relatively far from the interface. Similar flow patterns have been previously reported in literature for other impinging-jet geometries.

Figure 4:
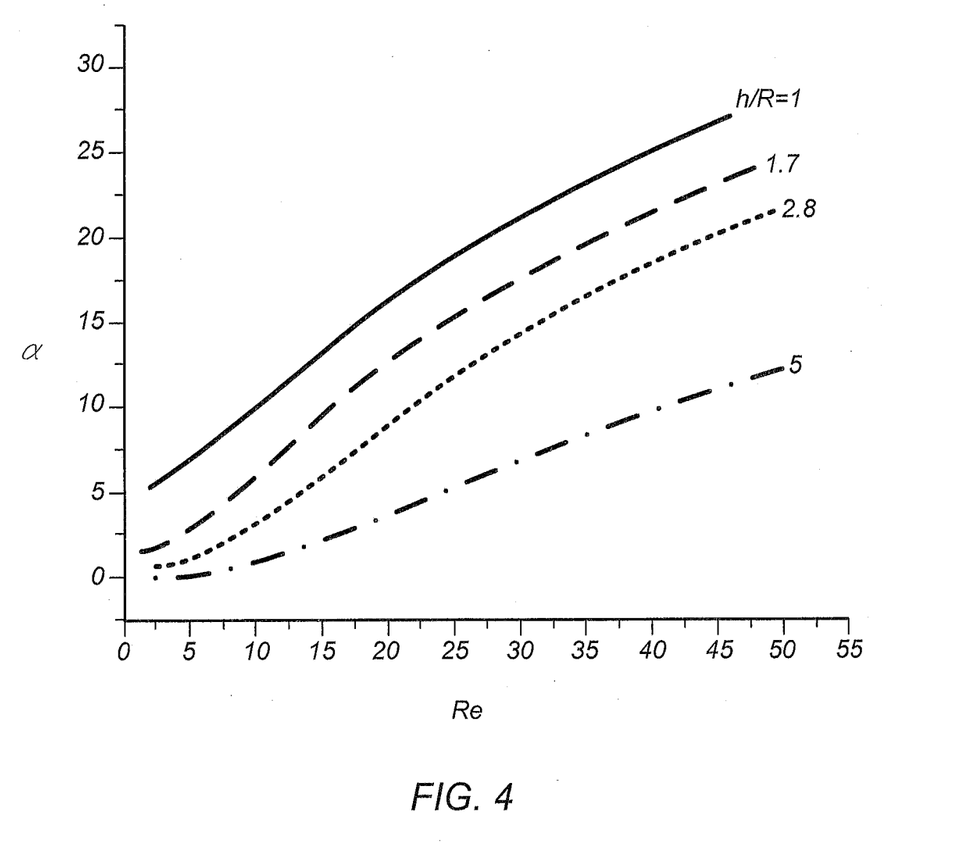
FIG. 4 depicts the dependence of the dimensionless parameter α with respect to Re for different flow cell designs.

The main advantage of performing adsorption experiments under stagnation point conditions is that the influence of hydrodynamic disturbances on the flow near the stagnation point can be eliminated. Although it has been generally reported that $\alpha$ is roughly proportional to Re, no information was available for the specific setting of our cell design (h/R=2.8). Consequently, to demonstrate that the described cell allows the development of stagnation flow conditions, the dependence of the dimensionless parameter $\alpha$ with respect to Re was calculated (see FIG. 4) for two different cell designs featuring h/R=2.8 and h/R=5 and compared to previously reported data for h/R=1 and h/R=1.7. As can be observed, the model herein described follows the same general trend that others previously reported. Although designs with large h/R values suffer from low mass-transfer efficiencies, the value selected for the cell herein described lays in the range of 1.5 to 4, which is considered optimum for adsorption kinetic measurements.

It is well-known that PEG readily adsorbs to a variety of materials with high affinity and with no significant energy barriers. Therefore, the adsorption of PEG is determined by the mass transfer rate from the bulk solution, making it reasonable to assume $\beta=1$. Consequently, the initial adsorption rate $((d\Gamma/dt)_{t \to 0})$ of PEG (as measured in our cell) should be equal to the flux of PEG to the surface (J), following Equation 14.

Figure 5:
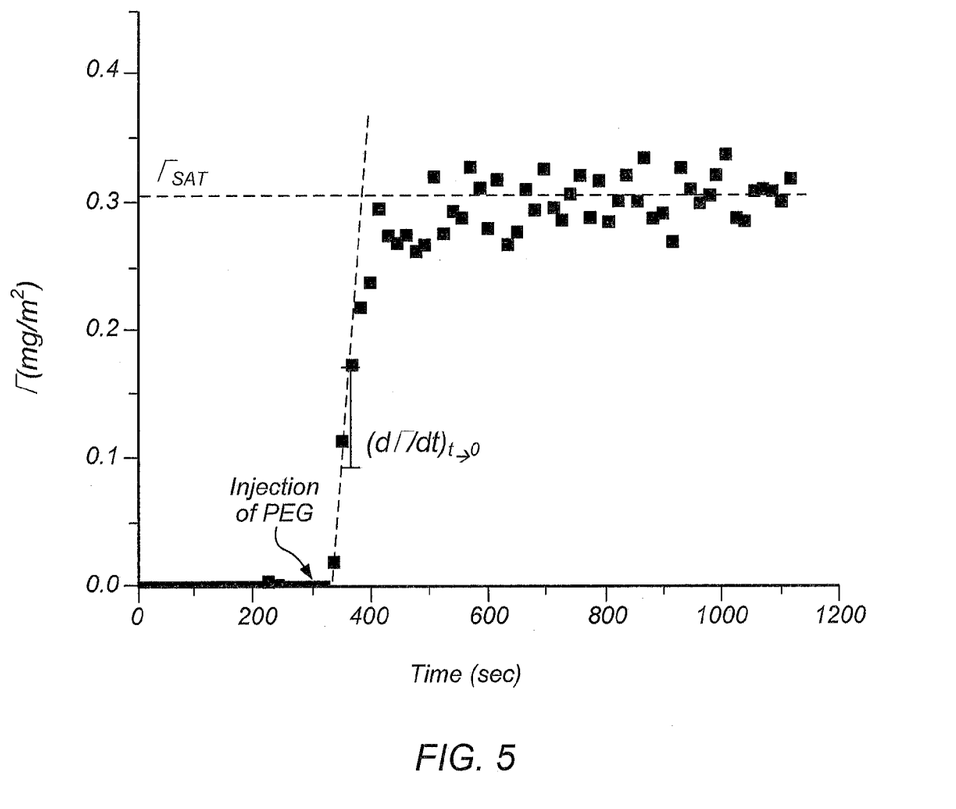
FIG. 5 depicts an example of a typical curve for adsorption of PEG onto $Si/SiO_2$ substrate.

A typical dynamic adsorption experiment is shown in FIG. 5. An initial fast adsorption process, followed by a slower one was always observed. Dynamic measurements (see FIG. 4) enabled calculating the initial adsorption rate $((d\Gamma/dt)_{t \to 0})$ under different experimental conditions. The results are summarized in FIG. 6, FIG. 7, and FIG. 8.

Figure 6:
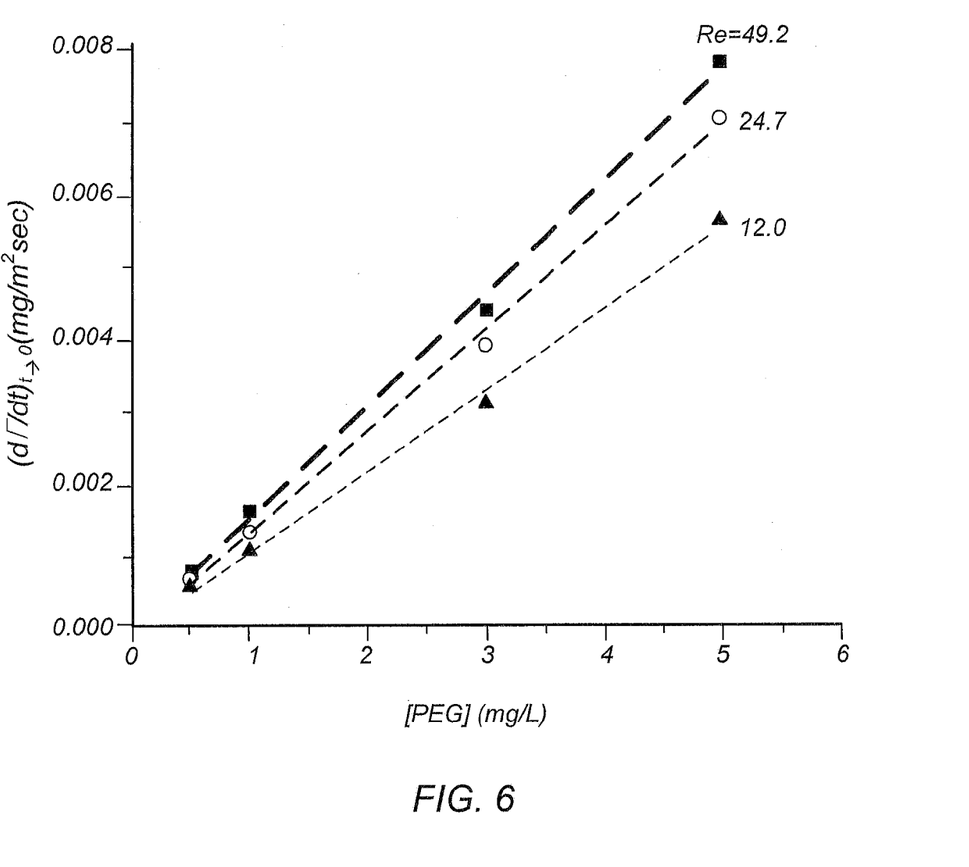
FIG. 6 depicts the initial adsorption rate of PEG as a function of the concentration for three Re numbers (93,000 g $mol^{-1}$)
Figure 7:
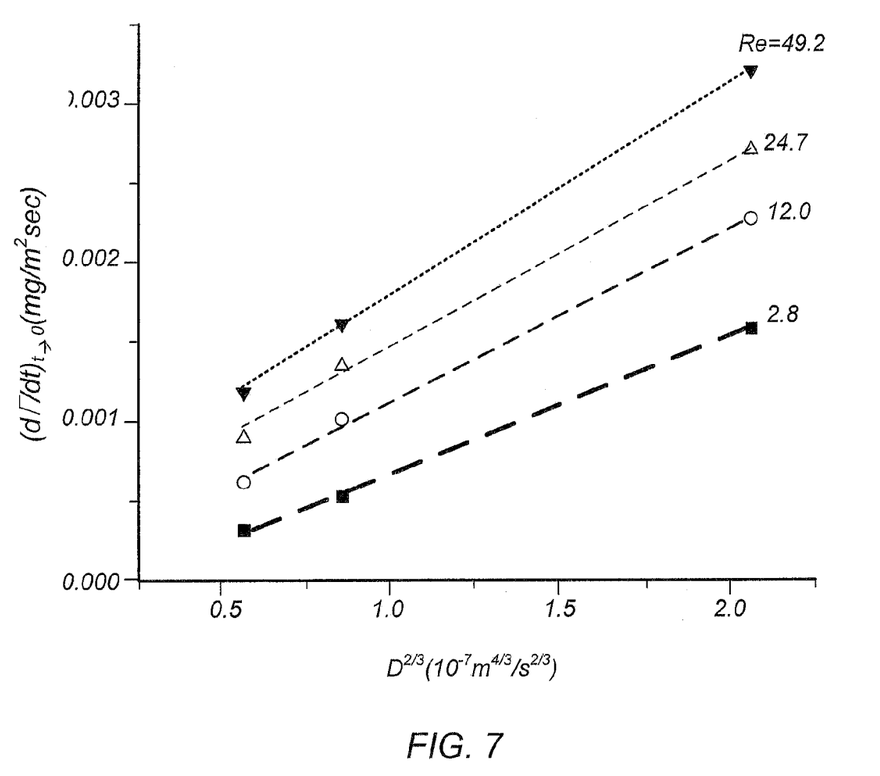
FIG. 7 depicts the initial adsorption rate of PEG as a function of the diffusion coefficient (c=1 mg $L^{-1}$)
Figure 8:
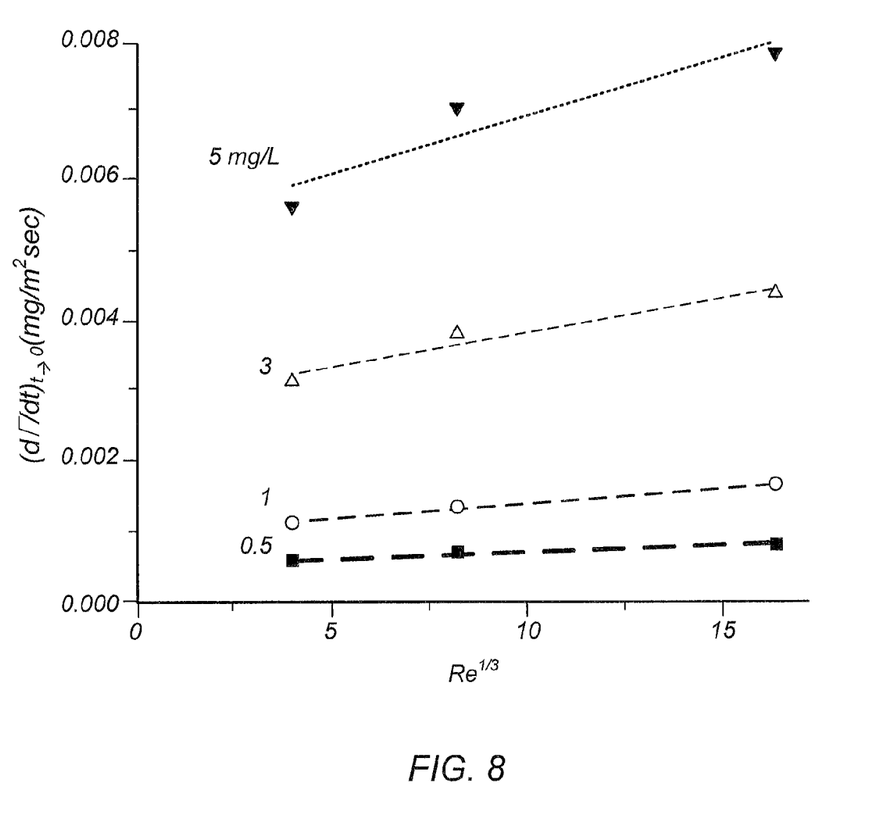
FIG. 8 depicts the initial adsorption rate of PEG as a function of the cube root of the Reynolds number for different PEG concentrations (Mw=93,000 g $mol^{-1}$)

As can be observed in FIG. 6, the initial rate of adsorption of PEG was proportional to the concentration of polymer in the impinging jet. FIG. 7 shows that a linear dependence between the initial adsorption rate and $D^{2/3}$ was obtained when polymers with different molecular weights (~8000 to 280000 g·mol$^{-1}$) were adsorbed (c=1 mg·L$^{-1}$). $\Gamma_{SAT}$ values of 0.16±0.02 mg·m$^{-2}$, 0.33±0.02 mg·m$^{-2}$, and 0.40±0.05 mg·m$^{-2}$ were obtained for PEG with molecular weights of 8730, 93000, and 278100 g·mol$^{-1}$, respectively. These results follow the general theory behind polymer adsorption which predicts an increase in $\Gamma_{SAT}$ for larger adsorbing molecules. Furthermore, as shown in FIG. 8, linear relationships between $(d\Gamma/dt)_{t \to 0}$ and Re$^{1/3}$ were obtained in the concentration range (0.5-5 mg·L$^{-1}$) studied.

In general, the initial adsorption rates obtained for our system were smaller than those previously reported with different cell setups (same polymer and h/R=1.6). This can be in part explained by the difference in h/R value. The higher h/R value selected for our cell implies a lower $\alpha$ (see FIG. 4) and, consequently, a lower rate of mass transfer. Furthermore, despite the fact that the experimental data obtained with our system followed the trends predicted by Equation 14, the initial adsorption rates were significantly lower than the flux of PEG towards the surface at the stagnation point (as predicted by Equation 14). It is necessary to note that the ellipsometer, as many other optical techniques, acquires data over a relatively large area compared to the infinitesimal stagnation point. In fact, the initial adsorption rates obtained by reflectometry (under stagnation point flow conditions and for transport limited adsorption processes) are only 50 to 80% of the theoretical values predicted by Equation 14. Because the local mass flux decreases significantly at interfacial points away from the stagnation point, the average mass transfer to the substrate decreases with increasing the area of measurement (compared to the stagnation point). Theoretical calculations using a circular spot rather than a point, demonstrated that the measurement over an area rather than at a point is indeed the source of deviation of experimental values from the theoretical ones for the stagnation point. In fact, it was shown that when the radius of the measured spot (r) equals to the radius of the inlet conduit (r/R=1), the experimentally obtained adsorption rates are only 90% and 70% of the flux at the stagnation point for Re of 1 and 48, respectively. The mentioned underestimation of the initial adsorption rates may be accounted for in the herein described system because the area of the measured spot is significantly larger (approximately 7 mm$^2$) than the values normally reported in literature for reflectometry (~1 mm$^2$). In fact, it was determined by computational dynamics that a reaches a value of approximately zero when the distance from the stagnation point (r) is greater than three times the radius of the impinging tube. It should be considered here that the estimated area of the measured spot in the ellipsometer comprise interfacial points that yield r/R>3 where $\alpha$ is actually very low. It is also worth noting that because $\alpha$ depends on Re, the errors in the experimental data are also Re dependent for a fixed area around the stagnation point. This fact complicates the comparison of the results obtained for different Re numbers even within the same experimental setup and, in turn, highlights the necessity of finding a setup-specific correction function. Such function would allow researchers to reasonably estimate the adsorption kinetics at the stagnation point and quantitatively compare their results even when using different cell setups and techniques.

Figure 9:
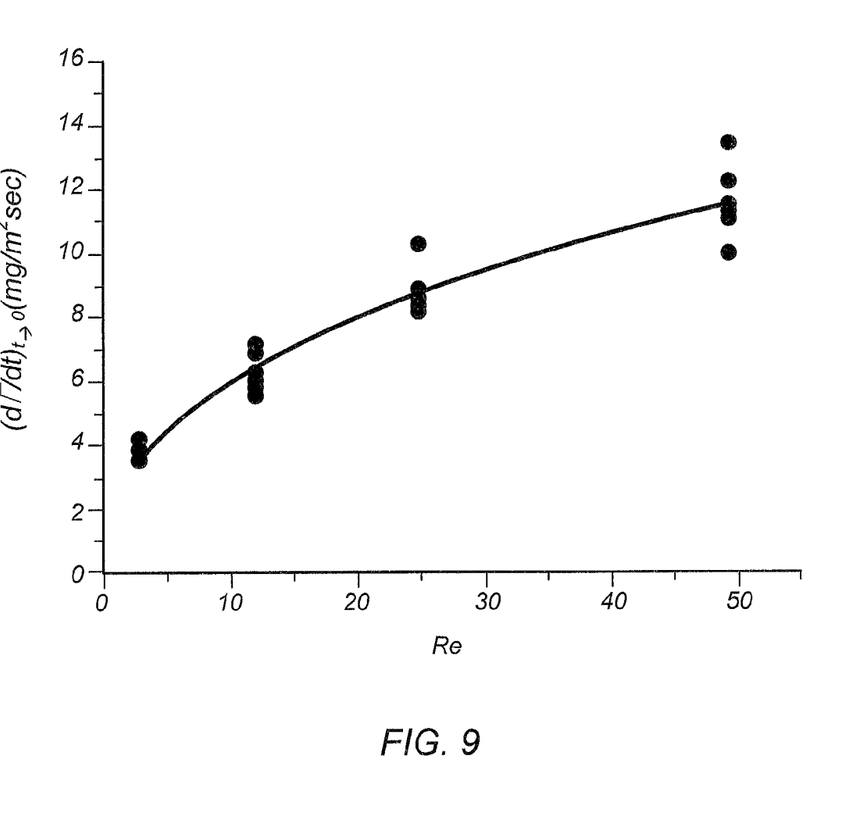
FIG. 9 depicts an analysis of the experimental initial adsorption rates ($(d\Gamma/dt)_{t\to 0}$) in relation to the theoretical values for flux predicted by Equation 14 ($J_{THEO}$) and Re.

In order to find such a function, the experimental initial adsorption rates $((d\Gamma/dt)_{t \to 0})$ were analyzed in relation to the theoretical values for flux predicted by Equation 14 ($J_{THEO}$). It was observed that, in agreement with previous reports from literature, the correction needed to account for the size of the measured spot is a function of Re. Subsequently, the ratio $J_{THEO}/(d\Gamma/dt)_{t \to 0}$ was assumed to be a simple power function of Re and the correction function (Equation 16) was empirically obtained from FIG. 9.

$$J_{THEO} \approx \left(\frac{d\Gamma}{dt}\right)_{Corrected} = \left(\frac{d\Gamma}{dt}\right)_{t \to 0} \times 2.3406 \times Re^{0.4094} \quad \text{Equation 16}$$

Figure 10:
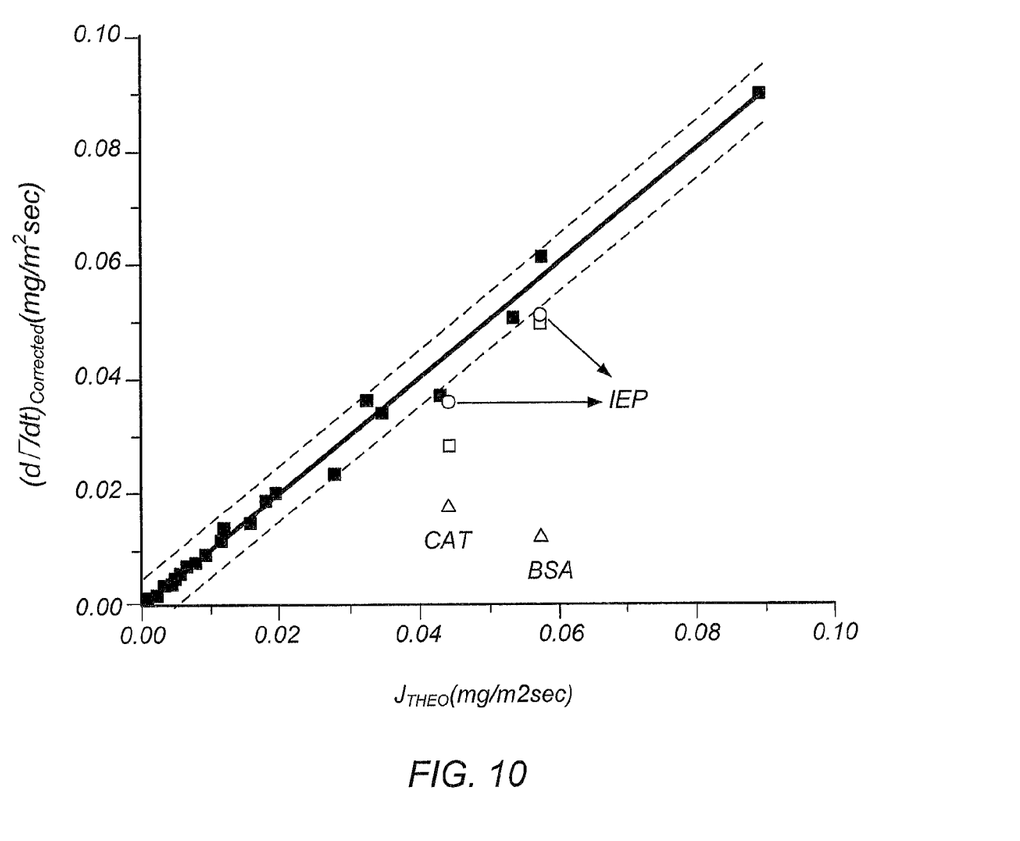
FIG. 10 depicts the corrected experimental values ($(d\Gamma/dt)_{Corrected}$) versus the theoretical flux ($J_{THEO}$) for PEG.

The corrected initial adsorption rates $((d\Gamma/dt)_{Corrected})$ provide a more realistic estimation of the adsorption kinetics at the stagnation point. It is worth noting that only experiments performed using adsorbates with well-known behavior (such as PEG, $(d\Gamma/dt)_{t \to 0}=J$) would allow the calculation of this function for a given set of experimental conditions. FIG. 10 shows the correlation between experimental values after applying the correction function $((d\Gamma/dt)_{Corrected})$ and the theoretical initial adsorption rates $(J_{THEO})$. As can be observed, a very good agreement between the two parameters was obtained (slope=1.00±0.02, $R^2$=0.9948) indicating that the correction is valid for all data points. It is also worth mentioning that this function would only be valid for the experimental setup used described in this paper. Any other cell with a specific geometry (h/R) and size of the measuring spot will generate data with different ratios and consequently, another expression of the correction function will be necessary.

In order to verify the applicability of the correction function to other analytes, the adsorption of two proteins (catalase and bovine serum albumin) with different molecular weights was studied (See Table 1). For these proteins, the initial adsorption rates obtained at pH values above, at, and below the isoelectric point were measured and corrected using Equation 16. It is well known that proteins exhibit different adsorption behavior depending on the pH of the solution because their net charge (and therewith the attachment probability) is affected by the pH. When the adsorbing analyte and the surface are both neutral or have opposite charges, there are no electrostatic barriers for the adsorption and, therefore, the initial adsorption rate should be larger than in the case when similar charges are present. In the latter case, the energy barrier is produced by the repulsion between the adsorbate and the sorbent surface. As can be observed in FIG. 10, the $(d\Gamma/dt)_{Corrected}$ for both proteins at the IEP fall within the 95% confidence interval predicted by Equation 16, resembling the adsorption rates obtained for PEG. These results suggest that under these conditions, the efficiency factor ($\beta$) is almost one. These results can be explained by considering that at the IEP, proteins do not have a net charge and therefore the electrostatic repulsion between the molecules and the surface is minimal. On the other side, the $(d\Gamma/dt)_{Corrected}$ obtained above the IEP was smaller than at the corresponding IEP probably due to electrostatic repulsion between the protein and the surface. Under these conditions, the adsorption rate after correction $(d\Gamma/dt)_{Corrected}$ is much smaller than the $J_{THEO}$ indicating a reduction in the efficiency factor ($\beta \ll 1$). At pH values below the IEP the results were different for the two proteins selected. For BSA, when the protein is positively charged, the initial adsorption rate is similar to the one obtained at the IEP because there is an attraction between the protein and the surface. These results are in agreement with previous reports. For catalase, at low pH values the $(d\Gamma/dt)_{Corrected}$ was smaller than the corresponding adsorption rate at the IEP. This result can be due to electrostatic repulsion between the protein molecules due to their high positive charge which also reduces the attachment efficiency. Similar results have been reported for other proteins on different surfaces.

It is evident from the results discussed here that the correction of the initial adsorption rates with the function obtained from PEG provides reasonable results. Thus, the correction function depends only on the cell setup and the instrumentation used, and does not depend specifically on the system under study.

Described herein is a flow cell that enables the investigation of adsorption processes under stagnation point flow conditions using spectroscopic ellipsometry. Theoretical calculations executed by computational fluid dynamics as well as adsorption experiments performed with PEG on $SiO_2$ support the existence of stagnation point flow in the cell design. In all cases, these results are consistent with previous reports stating that the adsorption of PEG to silica surfaces can be considered a fast process controlled by the transport of the adsorbate to the surface, rather than the transfer from the subsurface to the interface. In addition, the use of a setup-specific correction function that should be determined and applied to the experimental data in order to correct for the size of the measuring spot and for variations in mass transfer away from the stagnation point was proposed. This correction should allow quantitative comparisons of results obtained by different research groups using various techniques and experimental conditions. The validity of the correction function for other adsorbates was also demonstrated. In addition, the application of the mentioned correction allowed to distinguish between situations where $\beta \approx 1$ and where $\beta \ll 1$.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A device coupleable to a flow cell comprising:
an inlet conduit comprising an exit port, wherein the inlet conduit is configured to receive a fluid containing an adsorbate during use;
a substrate holder configured to couple to a substrate during use;
an inlet conduit positioner coupled to the inlet conduit;
wherein the exit port is positioned by the inlet conduit positioner such that fluid flows from the exit port toward the substrate during use and impinges the surface of a substrate, positioned in the substrate holder, at a point substantially coincident with light striking the substrate from a light inlet of the flow cell; and
wherein the inlet conduit positioner is configured to alter the distance of the exit port from the substrate and/or adjust the angle of the exit port with respect to the surface of the substrate.

2. The device of claim 1, wherein the fluid exits the exit port substantially perpendicular to the substrate during use.

3. The device of claim 1, wherein the inlet conduit positioner is configured to alter the distance of the exit port from the substrate.

4. The device of claim 1, wherein the inlet conduit positioner is configured to alter the angle between the exit port of the inlet conduit with respect to the surface to between about 0 degrees and about 90 degrees.

5. The device of claim 1, wherein the inlet conduit is positioned, with respect to the substrate, such that fluid exiting the exit port impinges the substrate creating a stagnation point.

6. The device of claim 1, wherein the flow cell is coupleable to an ellipsometer.

7. An ellipsometer comprising:
a light source;
a flow cell optically coupled to the light source;
a device coupled to the flow cell comprising:
   a substrate holder configured to couple to a substrate during use, wherein the light source is optically couplable to a substrate coupled to the substrate holder;
   an inlet conduit comprising an exit port, wherein the inlet conduit is configured to receive a fluid containing an adsorbate during use; and
   an inlet conduit positioner coupled to the inlet conduit;
   wherein the exit port is positioned by the inlet conduit positioner such that fluid flowing from the exit port to the substrate during use impinges the surface of a substrate, positioned in the substrate holder, at a point substantially coincident with light striking the substrate from a light inlet of the flow cell; and
   wherein the inlet conduit positioner is configured to alter the distance of the exit port from the substrate and/or adjust the angle of the exit port with respect to the surface of the substrate; and
a detector optically couplable to the substrate holder and the light source, wherein the detector receives light from the light source that is reflected from the substrate surface.

8. The ellipsometer of claim 7, wherein the fluid exits the inlet conduit substantially perpendicular to the substrate during use.

9. The ellipsometer of claim 7, wherein the inlet conduit positioner is configured to alter the distance of the exit port from the substrate.

10. The ellipsometer of claim 7, wherein the inlet conduit positioner is configured to alter the angle between the exit port of the inlet conduit with respect to the surface to between about 0 degrees and about 90 degrees.

11. The ellipsometer of claim 7, wherein the inlet conduit is positioned, with respect to the substrate, such that fluid exiting the exit port impinges the substrate creating a stagnation point.

12. A method of studying the adsorption of an adsorbate on a substrate comprising:
obtaining a flow cell;
coupling a device to the flow cell, the device comprising:
   an inlet conduit comprising an exit port, wherein the inlet conduit is configured to receive a fluid containing an adsorbate during use;
   a substrate holder configured to couple to a substrate during use; and
   an inlet conduit positioner coupled to the inlet conduit;
   wherein the exit port is positioned by the inlet conduit positioner such that fluid flows from the exit port toward the substrate during use and impinges the surface of a substrate, positioned in the substrate holder at a point substantially coincident with light striking the substrate from a light inlet of the flow cell; and
   wherein the inlet conduit positioner is configured to alter the distance of the exit port from the substrate and/or adjust the angle of the exit port with respect to the surface of the substrate;
sending a fluid containing the adsorbate through the inlet conduit toward a surface of a substrate disposed in the substrate holder, such that at least a portion of the fluid contacts the substrate;
sending light from a light source toward the position on the surface that is contacted by the fluid;
measuring the change in optical properties of light reflected from the substrate at the position on the surface that is contacted by the fluid.

13. The method of claim 12, wherein the fluid exits the exit port substantially perpendicular to the substrate.

14. The method of claim 12, further comprising adjusting the distance between the exit port and the substrate.

15. The method of claim 12, further comprising adjusting the angle between the exit port of the inlet conduit and the surface to be between about 0 degrees and about 90 degrees.

16. The method of claim 12, further comprising positioning the exit port, with respect to the substrate, such that fluid exiting the exit port impinges the substrate creating a stagnation point.

17. The method of claim 12, wherein the flow cell is coupled to an ellipsometer.

18. The method of claim 12, further comprising determining a correction factor to correct for specific parameters of the flow cell, wherein the correction factor is determined from the measured changes in optical properties of light reflected from the substrate at the position on the surface that is contacted by the fluid.

* * * * *